(12) United States Patent
Soler et al.

(10) Patent No.: US 7,718,100 B2
(45) Date of Patent: May 18, 2010

(54) DENTAL DEVICE AND METHOD TO MANUFACTURE THE SAME

(75) Inventors: Christoph Soler, Zwingen (CH); Ulrich Mundwiler, Tenniken (CH); Marco Wieland, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/070,455

(22) Filed: Mar. 2, 2005

(65) Prior Publication Data
US 2005/0266380 A1 Dec. 1, 2005

(30) Foreign Application Priority Data
Mar. 5, 2004 (EP) .................................. 04005302

(51) Int. Cl.
*A61C 13/00* (2006.01)
(52) U.S. Cl. ........................................................ 264/16
(58) Field of Classification Search ................. 433/233, 433/172–176; 264/16–20; 29/896.11
See application file for complete search history.

(56) References Cited

U.S. PATENT DOCUMENTS

| | | | |
|---|---|---|---|
| 5,052,931 A | 10/1991 | Kirsch | |
| 5,152,687 A * | 10/1992 | Amino | 433/173 |
| 5,167,502 A * | 12/1992 | Kawahara et al. | 433/173 |
| 5,358,402 A * | 10/1994 | Reed et al. | 433/8 |
| 5,482,671 A | 1/1996 | Weber | |
| 5,967,782 A * | 10/1999 | Shimodaira et al. | 433/173 |
| 6,066,274 A * | 5/2000 | Antonson et al. | 264/16 |
| 6,419,491 B1 | 7/2002 | Ricci et al. | |
| 2002/0160334 A1 | 10/2002 | Brodbeck | |
| 2003/0087217 A1* | 5/2003 | Coatoam | 433/173 |
| 2003/0113691 A1* | 6/2003 | Ben-Yaakov et al. | 433/220 |
| 2004/0038180 A1* | 2/2004 | Mayer et al. | 433/173 |

FOREIGN PATENT DOCUMENTS

| | | |
|---|---|---|
| EP | A-0 538 073 | 4/1993 |
| EP | A-0 820 737 | 1/1998 |
| WO | A 97/38811 | 10/1997 |

\* cited by examiner

*Primary Examiner*—Cris L Rodriguez
*Assistant Examiner*—Sunil K Singh
(74) *Attorney, Agent, or Firm*—Scully, Scott, Murphy & Presser, P.C.

(57) ABSTRACT

A dental device, in particular a dental implant, including an outer body made of ceramic or metal; and an inner body made of metal or ceramic, provided that when the outer body is made of metal the inner body is made of ceramic and when the outer body is made of ceramic the inner body is made of metal, wherein the metal body is produced by metal injection molding and the ceramic body is produced by ceramic injection molding as well as to a method for manufacturing the same.

21 Claims, 5 Drawing Sheets

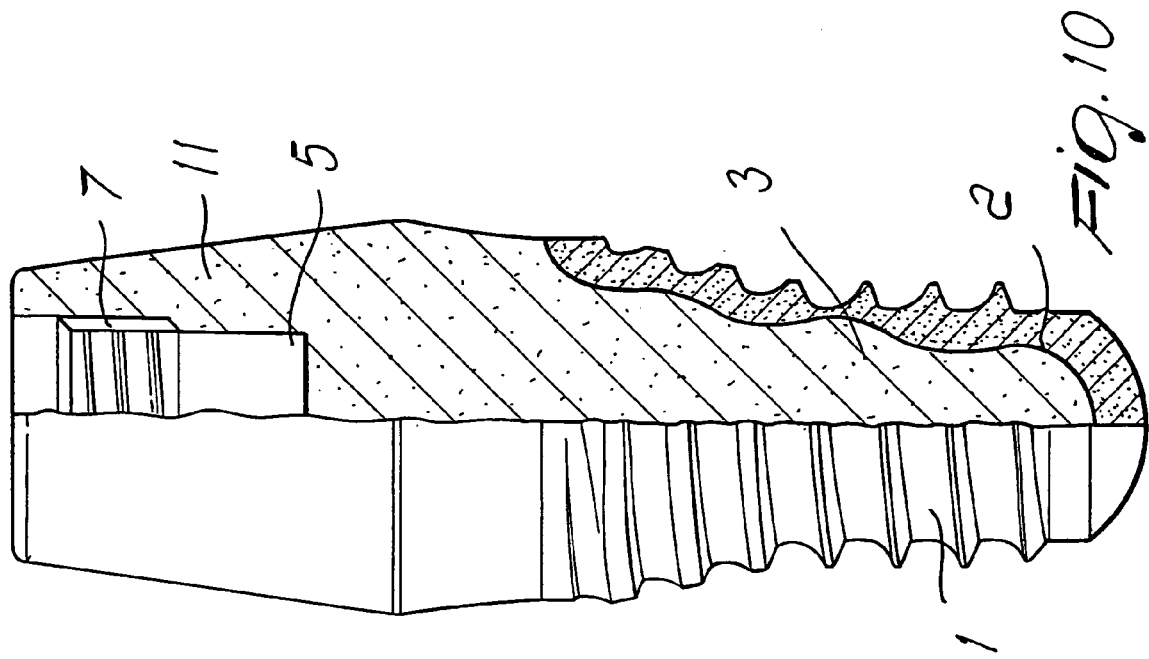
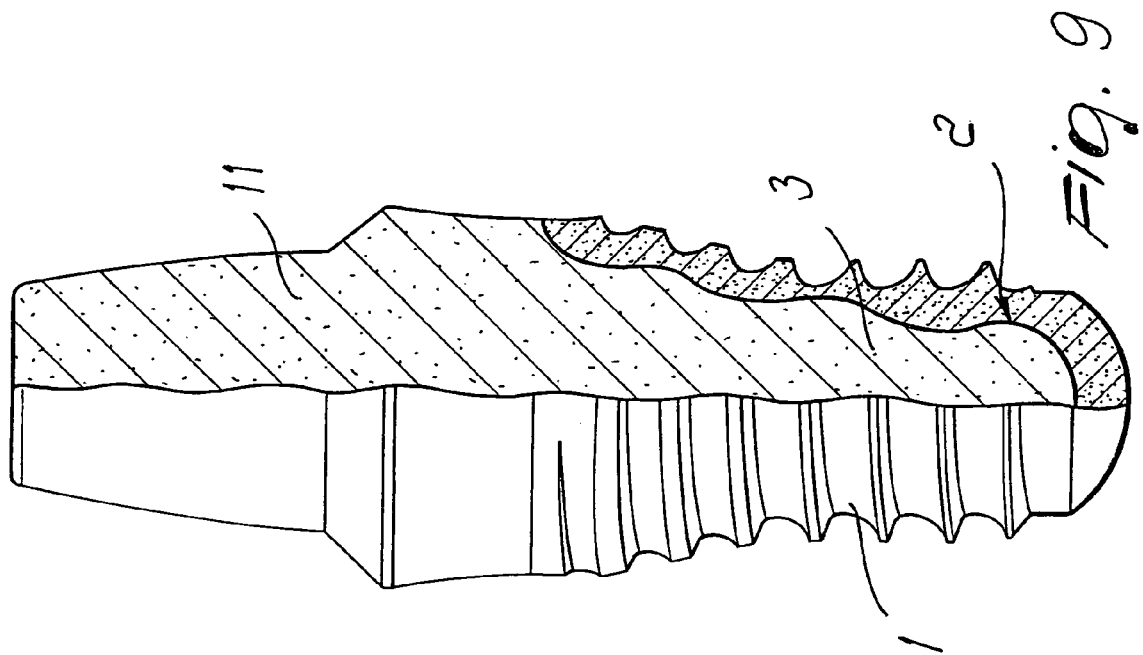

US 7,718,100 B2

DENTAL DEVICE AND METHOD TO MANUFACTURE THE SAME

The invention relates in general to a dental device and to a method to manufacture the same, and in particular to a dental implant and to a method to manufacture the same.

BACKGROUND OF THE INVENTION

Dental devices in general and dental implants in particular are nowadays made basically of two classes of materials: metals and ceramics.

With regards to metal, several metals are used for forming implants. Each metal has its own characteristic which renders the metal a possible suitable choice for the dental implants. For example, Ti (titanium) or titanium alloy are generally used. Titanium dental implants are relatively light, have high strength, and they have excellent corrosion resistance and bio-compatibility.

Alternatively ceramic materials such as zirconia-based, alumina-based and/or sapphire-based ceramics have been used for manufacturing dental implants or dental devices.

Dental devices, in general, and dental implants, in particular, formed from ceramic materials have the disadvantage that the material is more brittle as shown by a low value for the notched bar impact test. Ceramic materials are also susceptible to uncontrolled internal and external micro-cracks, and therefore they are prone to fail catastrophically. Moreover, artificial ceramic dental devices are rather expensive. However, the ceramic dental devices in general and the visible section of dental implants in particular, have a better aesthetic impact with respect to the metal implant and therefore enjoy a higher acceptance with the dental device bearer.

Furthermore, in some instances, a dental implant which is made of metal only may come into contact with an abutment/crown which is also made of a metal like for instance titanium, titanium alloy, gold or a gold alloy. Alternatively the abutment/crown is made of ceramic such as zirconia-based, alumina-based (for instance in-ceram®) and/or sapphire-based ceramics, or a ceramic glass composite. In the first metal to metal case, saliva or tissue fluid, acting as an electrolyte, may cause a galvanic electric current to flow which in extreme cases may have unpleasant effects for the dental prosthesis bearer. Also the metal, in particular if metals other than titanium are used in contact with a titanium implant, may cause inflammation and irritation of the soft tissue which it contacts.

In view of the above, there is the need of a dental device that combines the advantages of the metal made dental devices with those of the ceramic made dental devices and which can be easily manufactured.

Furthermore, in view of the foregoing, there is the particular need for a dental implant that combines the advantages of the metal made dental implants with those of the ceramic made dental implants and which can be easily manufactured.

SUMMARY OF THE INVENTION

The object of the present invention is to provide dental device such as dental implant, dental prosthesis and the like that are easy to manufacture and have good bio-compatibility, high strength and a good aesthetic impact.

In one preferred embodiment thereof the present invention is directed to a dental device, in particular a dental implant, which comprises an outer body made of ceramic or metal; and an inner body made of metal or ceramic, provided that when the outer body is made of metal the inner body is made of ceramic and when the outer body is made of ceramic the inner body is made of metal, wherein the metal body is produced by metal injection molding and the ceramic body is produced by ceramic injection molding.

Furthermore, in one embodiment of the present invention the inner/outer ceramic body is formed in a first step by ceramic injection molding and the metal body is formed/molded on or in the ceramic body.

Preferably the metal according to the present invention is titanium, titanium alloy or any other comparable materials. Preferably the ceramic material is an aluminum or zirconium or magnesium based ceramic material, such as aluminum oxide, zirconium oxide or magnesium oxide or combinations thereof. Preferably, according to the invention, the ceramic material is electrically insulating.

In the case that the present invention is embodied as an endosseous dental implant it may be comprised of a metal implant part which is to be implanted in a bone tissue, that implant part having a portion defining an outer body or a sheath thereof; and a ceramic inner body. Both bodies are manufactured by metal injection molding and ceramic injection molding, respectively. Furthermore, the ceramic inner body may comprise a core, a collar and a hollow. Again, preferably the metal is titanium or a titanium alloy or the like and the ceramic is an aluminum or zirconium or magnesium based ceramic material or an oxide thereof, alone or in combination. Additionally the endosseous dental implant may be provided with an inner titanium sleeve which provides means for fixing to an abutment, cap, crown etc. wherein the titanium inner sleeve is located in the hollow of the inner body. Nevertheless, the material of the inner and outer bodies may be inverted. Also the inner sleeve may be chosen among metal or ceramics and preferably manufactured by metal injection molding and ceramic injection molding, respectively.

The outer body of the dental implant according to the present invention is manufactured using a metal injection molding method or a ceramic injection molding method in dependence to the material chosen for the outer body. The inner body is manufactured using a ceramic injection molding method or a metal injection molding method in dependence of the material chosen for the inner body. It will be appreciated that when the inner body is made of ceramic the outer body is made of metal and vice-versa.

According to the present invention the ceramic body (either when outer or inner body) may be manufactured by ceramic injection molding firstly, the metal outer/inner body being directly formed via metal injection molding on or in the shaped ceramic body.

Preferably the ceramic body manufactured by ceramic injection molding is pre-sintered to a given shape before the metal is injected in the mold containing the ceramic body. Thereafter, the complete product including pre-sintered ceramic body and metal body is sintered.

Thus, the present invention provides preferably for a process for manufacturing dental devices, in particular endosseous dental implants comprising the steps of: manufacturing a ceramic body by means of ceramic injection molding; and manufacturing the metal body directly on or inside the ceramic body via metal injection molding.

It is believed that the adhesion and/or the interaction between the two bodies is improved by the combination of ceramic and metal injection molding used to manufacture the respective bodies.

In fact, if the metal is heated over the ceramic body it interacts with the ceramic body to ensure a better adhesion. Possible micro-movements between the outer and the inner bodies are then avoided because the two bodies perfectly fit and there is no micro gap therebetween.

BRIEF DESCRIPTION OF THE DRAWINGS

The foregoing and other objects, features, and advantages of the invention, as well as presently preferred embodiments thereof, will become more apparent from a reading of the following description, in connection with the accompanying drawings in which:

FIG. 9 is a perspective partially cut away view which shows an example of an one-piece dental device according to the present invention; and FIG. 10 is a perspective partially cut away view which shows an other example of an one-piece dental device according to the present invention, wherein the inner body of the dental implant is provided with an inner sleeve.

DESCRIPTION OF THE PREFERRED EMBODIMENTS

Ceramic injection molding (CIM) and metal injection molding (MIM) are well known technologies in the art of molding. Similar to plastic injection molding, a molten polymer (called binder) plus ceramic (CIM) or metal (MIM) powder paste are injected into a mold. The volume of the part is restricted to small components. The binder material is removed by either solvent extraction or controlled heating to above the volatilization temperatures and the so called green body is sintered.

Both CIM and MIM consist essentially of the following steps:
powder manufacture;
mixing or blending;
injection molding; and
preferably sintering.

According to the knowledge of the present inventors, the two technologies have never been utilized together in order to form any kind of devices in general or dental devices and dental implants, respectively, in particular made up with ceramic and metal components/bodies.

The present invention will be exemplified disclosing an endosseous dental implant which is envisaged as the currently preferred embodiment thereof. However, it should be understood that the basic principles of the present invention (which includes the combination of metal injection molding and ceramic injection molding techniques) may be applied to other medical/dental devices like for instance dental prosthesis or to prosthetic parts in general. Also, it is believed that the basic principles of the invention are applicable to other non-medical devices.

Figure 1:
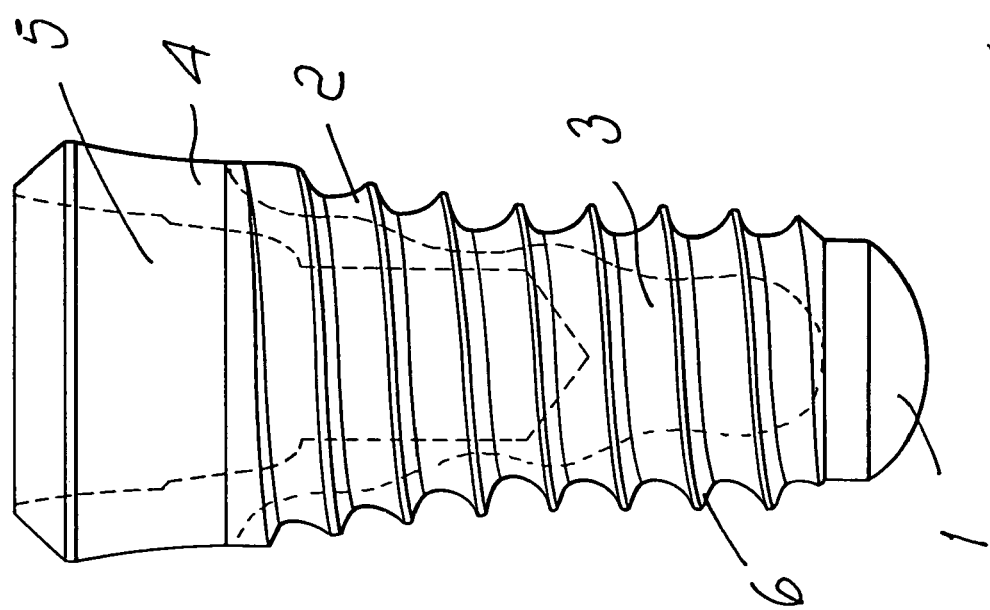
FIG. 1 is a cross sectional view which shows an example of the structure of a dental implant according to the present invention.
Figure 4:
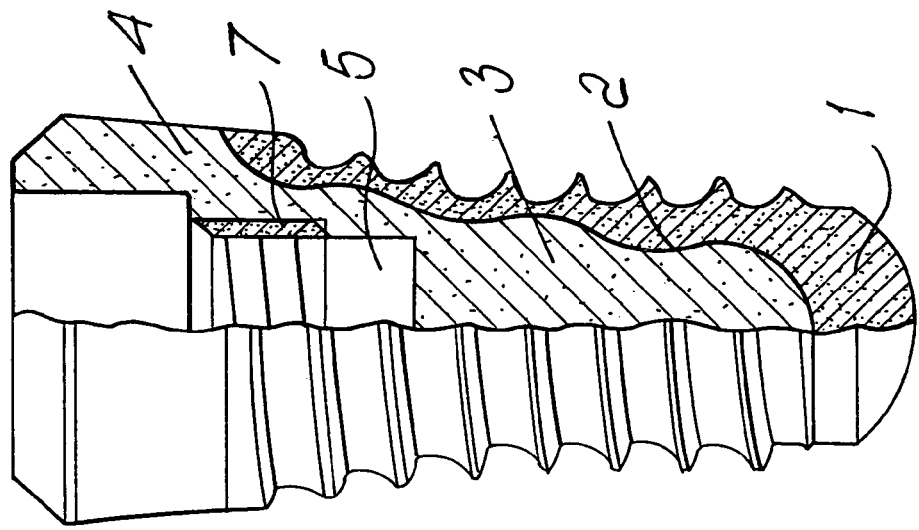
FIG. 4 is a perspective partially cut away view which shows an example of another dental implant according to the present invention, wherein the inner body of the dental implant is provided with an inner sleeve.
Figure 3:
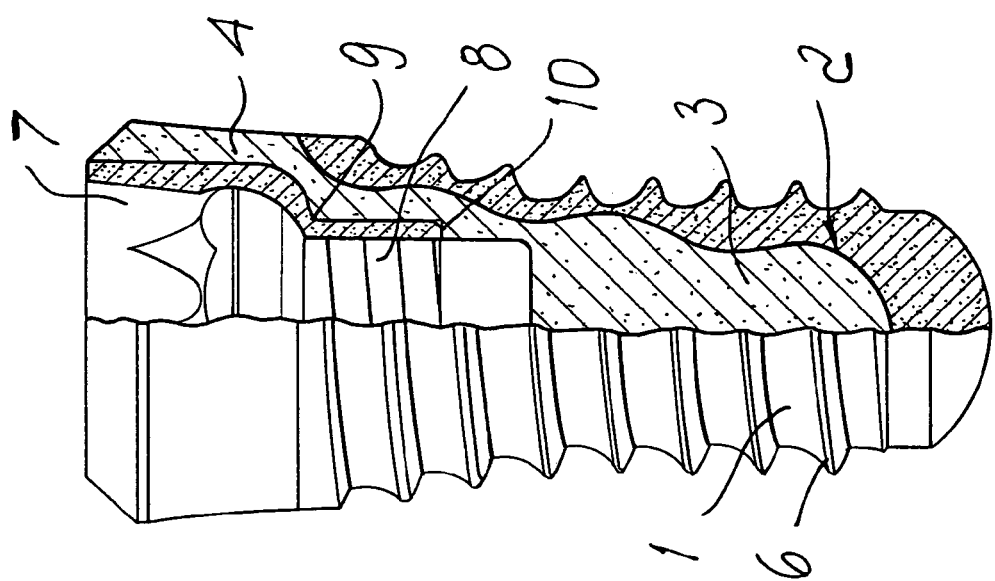
FIG. 3 is a perspective partially cut away view which shows the complete dental implant of FIG. 2, wherein the inner body of the dental implant is provided with the inner sleeve.
Figure 6:
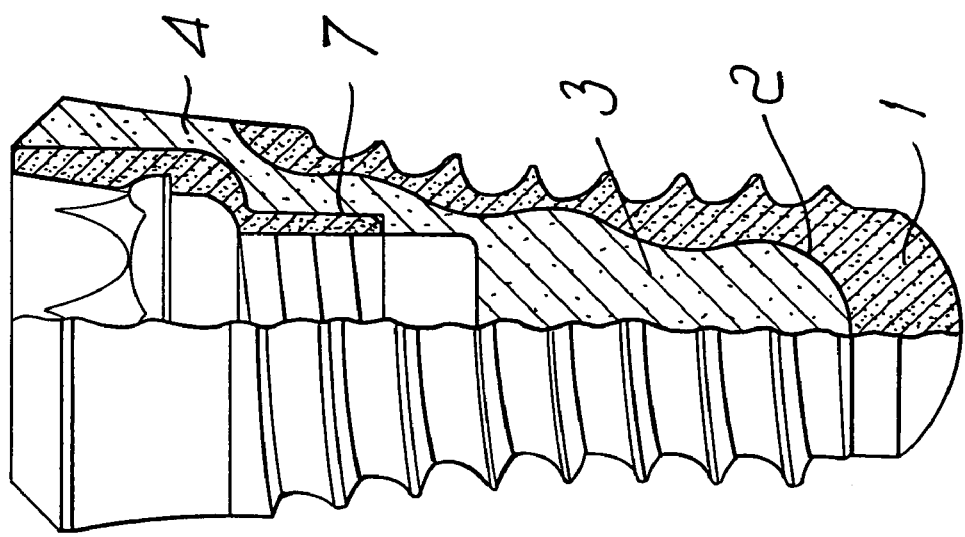
FIG. 6 is a perspective partially cut away view which shows an example of a further dental implant according to the present invention, wherein the inner body of the dental implant is provided with an inner sleeve.
Figure 5:
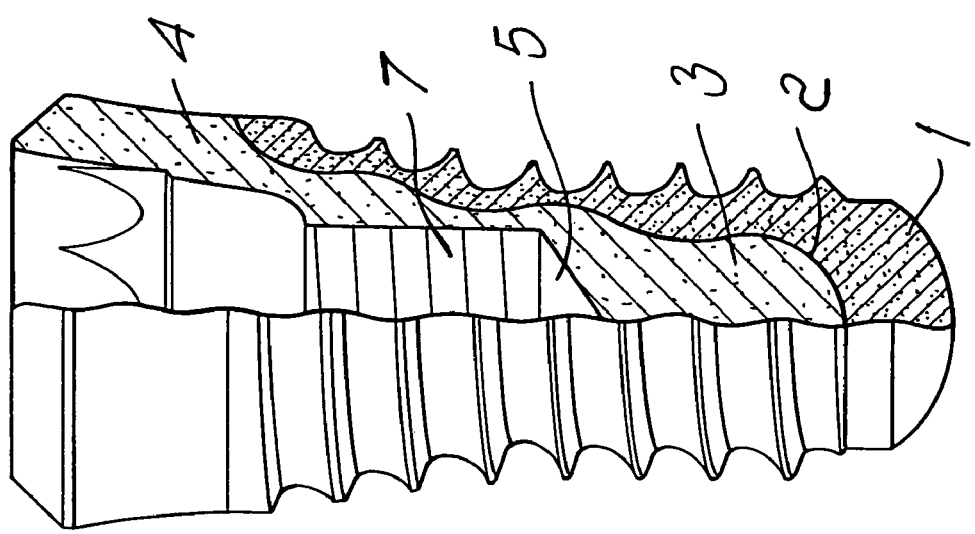
FIG. 5 is a perspective partially cut away view which shows an example of yet another dental implant according to the present invention, wherein the inner body of the dental implant is provided with an inner sleeve.
Figure 8:
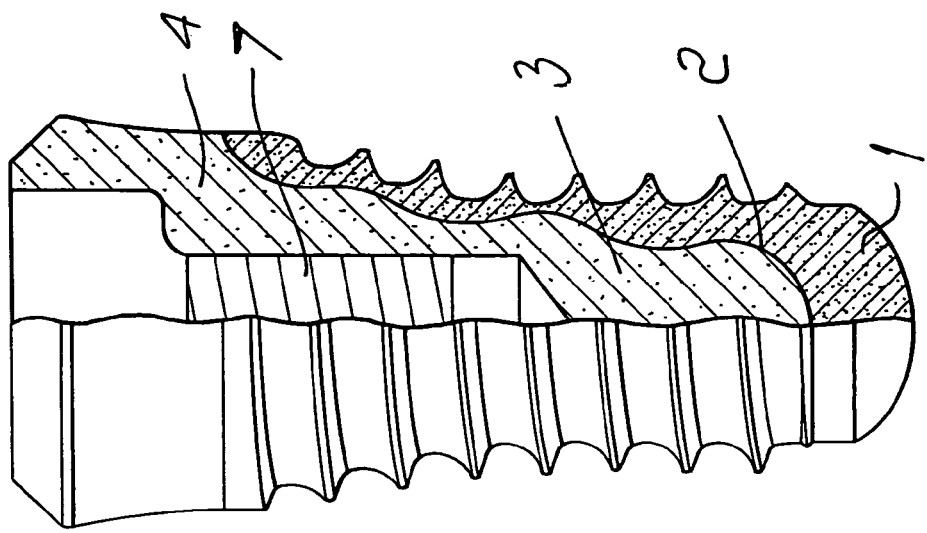
FIG. 8 is a perspective partially cut away view which shows an example of a modified dental implant according to the present invention, wherein the inner body of the dental implant is provided with an inner sleeve.
Figure 7:
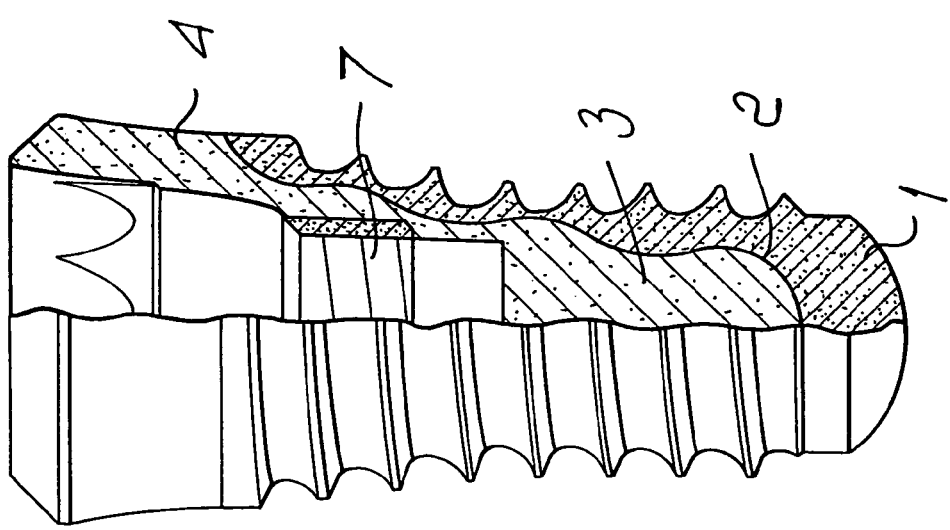
FIG. 7 is a perspective partially cut away view which shows an example of yet a further dental implant according to the present invention, wherein the inner body of the dental implant is provided with an inner sleeve.

The endosseous dental implant of the present invention, as shown in a schematic representation of FIG. 1, comprises a metal implanting part or outer body 1 which is to be implanted in bone tissue and a ceramic inner body 2 comprising a core 3, a collar 4 and a hollow 5. As well known in the relevant art, the metal implanting part or outer body 1 may be preferably provided with an external thread structure 6. Furthermore, the section of the outer body 1 in contact with the bone tissue may be treated to give it a special surface morphology or chemical properties preferably by sandblasting and/or acid-etching (for instance by the SLA—Sand-blasted, Large grit, Acid-etched—surface treatment method). Also titanium plasma spraying thereof is intended to be within the scope of the invention. Preferably sandblasting is performed with glass beads or $Al_2O_3$ grits or $TiO_2$ grits. The surface of the implant in contact with the gingival tissue may be advantageously polished, but other surface treatments to improve soft tissue attachment are possible. In addition, surface modification at the soft tissue and/or bone tissue apposition surface can be done by growth factor adsorption, and/or peptide adsorption, and/or protein adsorption, and/or amino acid adsorption. The SLA-interface may be designed advantageously to follow the outline of the tissue and is not necessarily identical to the interface between the inner body 2 and the outer body 1.

The inner shape/profile of the implanting part 1 (outer body) is complementary to the outer profile of the inner body 2.

Preferably, according to the invention, the inner profile of the implanting part or the outer body 1 is a rounded profile to decrease tension between the inner and the outer bodies. This complementary rounded profile is particularly advantageous as the present inner and outer bodies are manufactured by means of CIM and MIM, respectively.

The metal implanting part or the outer body 1 is made preferably of titanium or a titanium alloy or any other comparable materials. The inner body 2 is preferably an aluminum or zirconium or magnesium based ceramic material such as aluminum oxide, zirconium oxide or magnesium oxide or combinations thereof. Preferably, the ceramic material is electrically insulating.

The inner body 2 comprises the core 3 which lies inside the outer body 1. The outer profile of the inner body 2 has, as explained, a rounded profile which is complementary to the inner profile of the outer body 1, such that the rounded profile alleviates the tension between the outer body 1 and the inner body 2. The profile may also advantageously be adapted for locking against relative rotation of the two bodies. Thus, the profile includes an anti-rotation feature.

Further the inner body 2 is provided with the collar 4 which is located at the distal end thereof. The collar 4 is, in the implanted state, basically in contact with the soft tissue, such that to avoid direct contact of the metal outer body 1 with the soft tissue.

As shown in FIGS. 2 through 8 the dental implant may optionally be provided with a titanium inner sleeve 7 which provides for a fixing to an abutment, cap, crown etc. (not shown), wherein the titanium inner sleeve 7 is located in the hollow 5 defined at the collar 4 of the inner body 2. Otherwise the dental implant of FIGS. 2 through 8 incorporates the features described in connection with FIG. 1.

Figure 2:
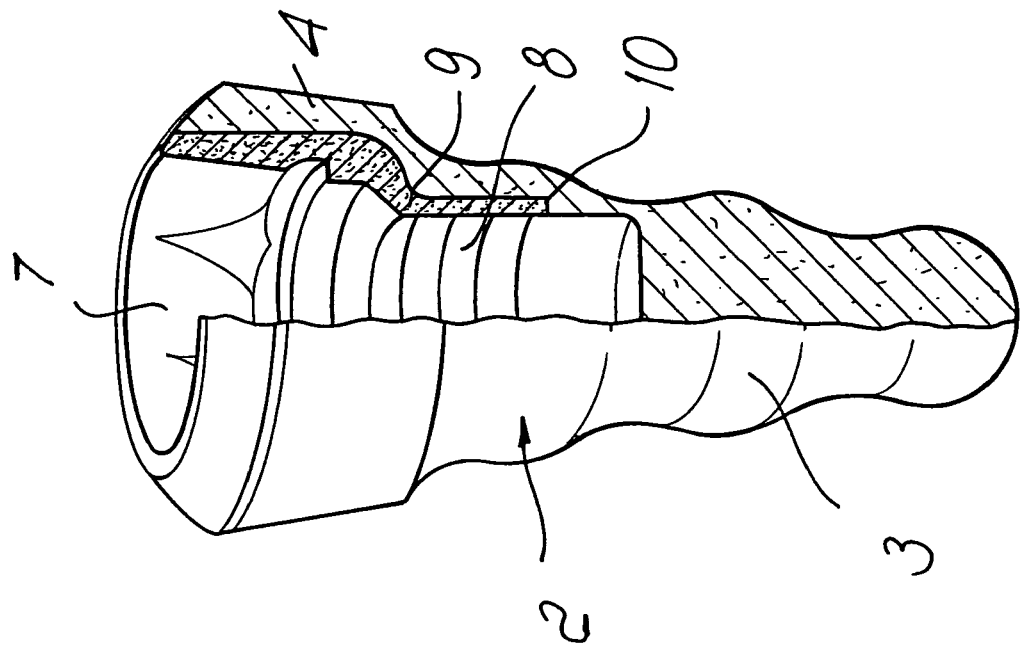
FIG. 2 is a perspective partially cut away view which shows an example of an inner body of a dental implant according to the present invention, wherein the inner body is provided with an inner sleeve.

Preferably, the inner sleeve 7 of the FIG. 2 is provided in a known manner with a thread 8 and anti-rotation means 8' (for instance of polygonal, octagonal or any other suitable shape) for fixing the abutment, cap, crown etc (not shown). The inner sleeve 7 is snap coupled to the inner body 2 with corresponding means indicated at reference numeral 9. A gap 10 may be formed at the interface between the sleeve 7 and the lower section of the hollow 5 of the inner body 2.

As indicated in FIGS. 4 through 8 the snap coupling 9 between the inner body 2 and the sleeve 7 may be left out and instead a press fitting, an adhesive coupling, lock engagement, warm shrinking may be provided. Also it is conceivable according to the present invention to provide combinations of two or more of snap coupling, press fitting, adhesive coupling, lock engagement and warm shrinking between the sleeve and the inner body 2. Furthermore, the sleeve 7 may also be provided by means of a MIM process if it is made of metal or by a CIM process if ceramics are used. The vertical length of the hollow 5 may vary according to the length of the thread 8 of the sleeve 7 and the anti-rotation means 9' may be omitted.

As shown in FIGS. 9 and 10 the dental device according to the present invention may be designed as an one-piece device including the outer body 1 and the inner body 2, the inner body 2 forming at an upper section thereof an abutment 11. The one-piece dental device of FIG. 10 is formed in a similar manner to the implant of FIGS. 2 through 8 with a titanium inner sleeve 7, the titanium inner sleeve 7 being located in the hollow 5 defined at the abutment 11 of the inner body 2. Otherwise the dental device of FIGS. 9 and 10 incorporates the features described in connection with FIG. 1 and therefore such features will not be repeated. Also the inner sleeve 7 may be designed in the same manner as the inner sleeve described in connection with FIGS. 2 through 8.

The dental implants or dental devices of the present invention, as shown in FIGS. 1 through 10, are manufactured by means of a combination of a CIM/MIM method which process is part of the present invention.

The manufacturing of the ceramic inner body 2 is accomplished according to a CIM method by injecting the powdered ceramics into shaped molds. The ceramic is provided as powdered material. It contains binder for better molding or forming; the binder is preferably removed after forming by burning it out prior to sintering. The shaped ceramic inner body is preferably subsequently pre-sintered.

The metal outer body 1 is then preferably formed/molded on the ceramic inner body 2. When the metal outer body 1 is made on the ceramic inner body 2, preferably the sintered ceramic inner body 2 is moved to another shaped mold wherein it undergoes the MIM process. Thereafter, the complete product including the CIM made inner body and the MIM made outer body is sintered in a final sintering step.

The pre-sintering step of the CIM inner body is intended to give the inner body a final shape, and therefore problems of different expansion coefficients of ceramics and metal during the final sintering step may be avoided.

It will be appreciated that according to the invention the inner body may be made of metal by a MIM process and the outer body of ceramic by a CIM process. In this case, preferably, the metal inner body is molded into the ceramic outer body. It will be further appreciated that when the metal inner body is molded inside the ceramic outer body the mold for the metal component may be construed inside the ceramic body. Same applies if the sleeve 7 is made by metal injection molding inside the inner body.

The metal body is formed/molded on a pre-formed ceramic body. Because of the process the two bodies are perfectly shaped.

The embodiments described are chosen to provide an illustration of principles of the invention and its practical application to enable thereby the person of ordinary skill in the art to utilize the invention in various embodiments and with various modifications as are suited to the particular use contemplated. Therefore, the foregoing description is to be considered exemplary, rather than limiting, and the true scope and spirit of the invention is that described in the appended claims.

The disclosures in European Patent Application No. 04005302.7 from which this application claims priority are incorporated herein by reference.

What is claimed is:

1. A method for manufacturing a dental implant for endosseous implantation, comprising a ceramic and a metal body, wherein the method comprises the following steps:
   manufacturing the ceramic body via ceramic injection molding;
   manufacturing the metal body via metal injection molding, the ceramic body being manufactured prior to the metal body, and the metal body being manufactured directly on or inside the ceramic body via metal injection molding; and
   pre-sintering the ceramic body prior to the manufacturing of the metal body.

2. The method of claim 1, further comprising the step of sintering both the ceramic and metal body.

3. The method of claim 1, wherein the dental implant has the ceramic body as an inner body and the metal body as an outer body.

4. The method of claim 3, wherein the dental implant further includes an inner sleeve within a hollow of the inner body, the inner sleeve being adapted for providing fixing means to an abutment, cap, crown or the like, and further comprising the step of fixing the inner sleeve to the hollow of the inner body by one or more of the steps of snap coupling, press fitting, adhesive coupling, lock engagement and warm shrinking.

5. The method of claim 4, wherein the inner sleeve is provided by a step of a metal injection molding or ceramic injection molding.

6. The method of claim 1, wherein the metal is selected among titanium or a titanium alloy, and the ceramic is selected among zirconia-based, alumina-based and/or sapphire-based ceramic.

7. The method of claim 1, further including the step of forming the inner profile of the outer body complementary to the outer profile of the inner body, and wherein preferably the respective profiles are rounded, such as to decrease tension between the inner and the outer bodies and/or such that to provide for an anti-rotation lock between the two bodies 8. The method of claim 1, wherein the dental device is an one-piece dental device and further including the step of manufacturing an abutment integral with one of the metal or the ceramic bodies.

9. The method of claim 8, further including the step of providing an inner sleeve within a hollow of the abutment, the inner sleeve being adapted for providing fixing means to a cap, crown or the like, and further comprising the step of fixing the inner sleeve to the hollow of the inner abutment by one or more of the steps of snap coupling, press fitting, adhesive coupling, lock engagement and warm shrinking.

10. The method of claim 1, further comprising the step of topographically or chemically modifying the implant surface by one or more processes selected from the group consisting of: sand blasting, acid-etching, plasma spraying, growth factor adsorption, peptide adsorption, protein adsorption, and amino acid adsorption, and wherein the modification of the implant surface is carried out at at least one of a soft tissue and a bone tissue apposition surface.

11. A method for manufacturing a dental implant for endosseous implantation, comprising a ceramic and a metal body, wherein the method comprises the following steps in any order:
- manufacturing the ceramic body via ceramic injection molding;
- manufacturing the metal body via metal injection molding, the ceramic body being manufactured prior to the metal body; and
- pre-sintering the ceramic body prior to the manufacturing of the metal body.

12. The method of claim 11, wherein, the metal body is manufactured directly on or inside the ceramic body via metal injection molding.

13. The method of claim 11, further comprising the step of sintering both the ceramic and metal body.

14. The method of claim 11, wherein the dental implant has the ceramic body as an inner body and the metal body as an outer body.

15. The method of claim 14, wherein the dental implant further includes an inner sleeve within a hollow of the inner body, the inner sleeve being adapted for providing fixing means to an abutment, cap, crown or the like, and further comprising the step of fixing the inner sleeve to the hollow of the inner body by one or more of the steps of snap coupling, press fitting, adhesive coupling, lock engagement and warm shrinking.

16. The method of claim 15, wherein the inner sleeve is provided by a step of a metal injection molding or ceramic injection molding.

17. The method of claim 11, wherein the metal is selected among titanium or a titanium alloy, and the ceramic is selected among zirconia-based, alumina-based and/or sapphire-based ceramic.

18. The method of claim 11, further including the step of forming the inner profile of the outer body complementary to the outer profile of the inner body, and wherein preferably the respective profiles are rounded, such as to decrease tension between the inner and the outer bodies and/or such that to provide for an anti-rotation lock between the two bodies 19. The method of claim 11, wherein the dental device is an one-piece dental device and further including the step of manufacturing an abutment integral with one of the metal or the ceramic bodies.

20. The method of claim 19, further including the step of providing an inner sleeve within a hollow of the abutment, the inner sleeve being adapted for providing fixing means to a cap, crown or the like, and further comprising the step of fixing the inner sleeve to the hollow of the inner abutment by one or more of the steps of snap coupling, press fitting, adhesive coupling, lock engagement and warm shrinking.

21. The method of claim 11, further comprising the step of topographically or chemically modifying the implant surface by one or more processes selected from the group consisting of: sandblasting, acid-etching, plasma spraying, growth factor adsorption, peptide adsorption, protein adsorption, and amino acid adsorption; and
- wherein the modification of the implant surface is carried out at at least one of a soft tissue and a bone tissue apposition surface.

* * * * *